United States Patent
Lemonnier

(10) Patent No.: US 6,776,294 B2
(45) Date of Patent: Aug. 17, 2004

(54) DEVICE FOR MICROBIOLOGICAL EXAMINATION OF A SAMPLE OF LIQUID UNDER PRESSURE AND METHOD FOR DRAINING THIS DEVICE

(75) Inventor: Jean Lemonnier, Paris (FR)

(73) Assignee: Millipore Corporation, Billerica, MA (US)

( * ) Notice: Subject to any disclaimer, the term of this patent is extended or adjusted under 35 U.S.C. 154(b) by 0 days.

(21) Appl. No.: 10/089,533

(22) PCT Filed: Dec. 18, 2000

(86) PCT No.: PCT/IB00/01902

§ 371 (c)(1),
(2), (4) Date: Mar. 27, 2002

(87) PCT Pub. No.: WO01/48141

PCT Pub. Date: Jul. 5, 2001

(65) Prior Publication Data

US 2002/0192739 A1 Dec. 19, 2002

(51) Int. Cl.[7] .............................................. B01D 35/00
(52) U.S. Cl. ..................... 210/406; 210/416.1; 210/435; 210/455; 210/466; 210/321.84; 422/101; 435/308.1
(58) Field of Search .............................. 210/321.6, 644, 210/645, 650, 651, 288, 321.75, 321.84, 244, 416.1, 406, 473, 474, 477, 464, 498; 422/101, 102, 104; 435/30, 287.9, 288.1, 297.1, 297.2, 297.5, 308.1

(56) References Cited

U.S. PATENT DOCUMENTS

| 4,319,996 A | | 3/1982 | Vincent et al. |
| 4,614,585 A | * | 9/1986 | Mehra et al. .......... 210/321.81 |
| 4,678,576 A | | 7/1987 | Leoncavallo |
| 5,288,638 A | * | 2/1994 | Lemonnier ............... 435/287.1 |
| 5,308,483 A | | 5/1994 | Sklar et al. |
| 5,688,460 A | | 11/1997 | Ruschke |

FOREIGN PATENT DOCUMENTS

| EP | 0059809 | 9/1982 |
| EP | 0319701 | 6/1989 |

* cited by examiner

Primary Examiner—W. L. Walker
Assistant Examiner—Krishnan S Menon
(74) Attorney, Agent, or Firm—John Dana Hubbard

(57) ABSTRACT

This concerns a device whose filtering membrane is gripped annularly at the periphery between a first member forming part of an intake body and a second member forming part of a drainage body with one out of the first member and second member having an elastomer seal by means of which it comes into contact with the membrane, and whose locking means are adapted to allow the opening of the device by requiring only a separation movement between said first member and said second member. The drainage method proposes directly placing the device on a vacuum flask, the sealing with regard to the stopper of said flask being obtained by a rib tapering towards its end.

28 Claims, 7 Drawing Sheets

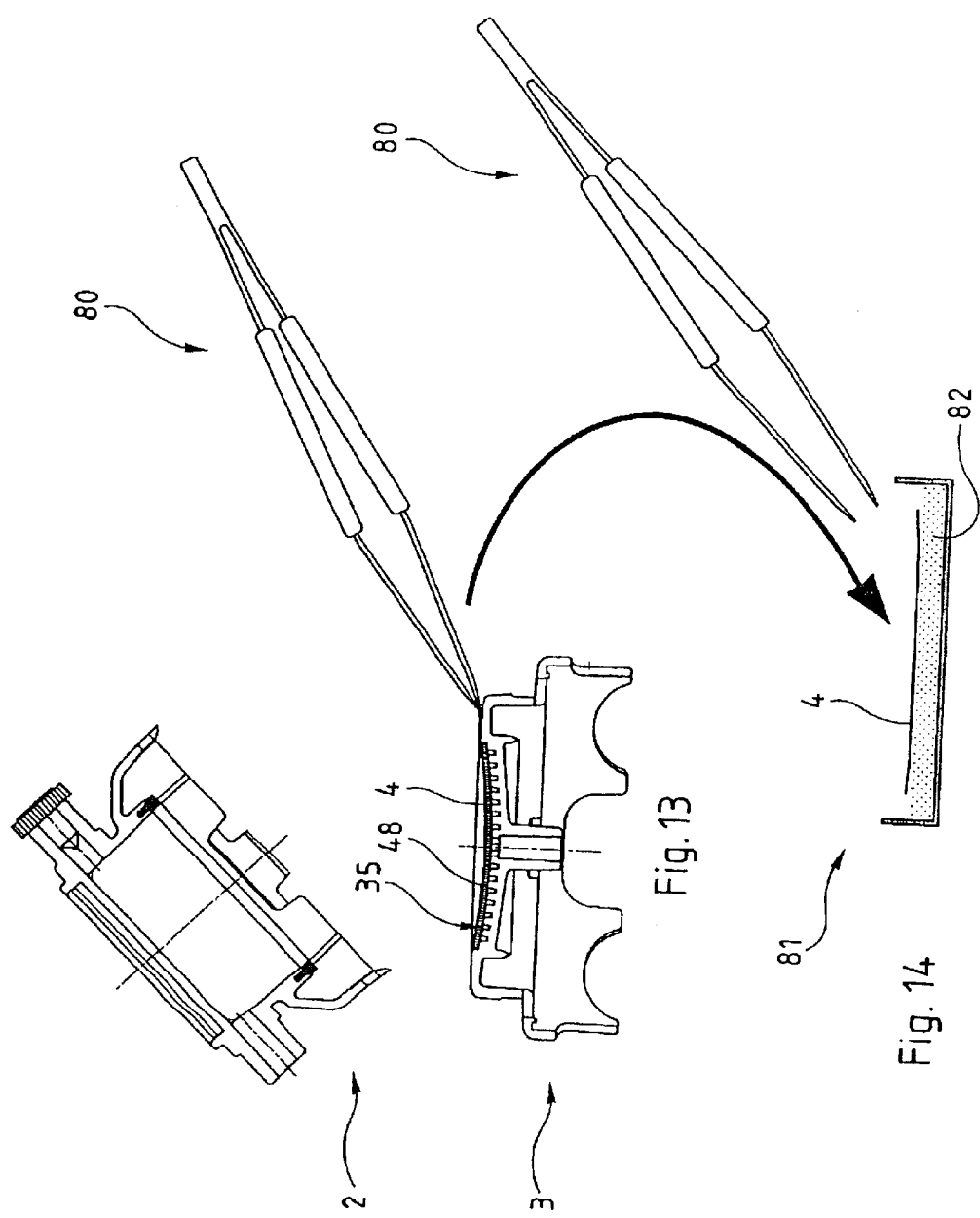

DEVICE FOR MICROBIOLOGICAL EXAMINATION OF A SAMPLE OF LIQUID UNDER PRESSURE AND METHOD FOR DRAINING THIS DEVICE

The invention relates to the devices for microbiological examination of a sample of liquid under pressure.

Such a device is already known through French patent 2 677 664, having an intake body, a filtering membrane and a drainage body. The intake body has a reservoir, in one wall of which a liquid input aperture is made, the membrane closing this reservoir by being welded on to the edge of the lateral wall of this reservoir, the drainage body being designed to support the membrane on the opposite side from the reservoir and being provided with a liquid output aperture, the intake body and the drainage body locking with one another by screwing by virtue of integrally moulded thread elements.

The taking of a sample to be examined is performed by connecting the input aperture of the reservoir of the intake body to a source of liquid under pressure, so that the reservoir fills with this liquid, which can leave therefrom only through the filtering membrane, this liquid being recovered from the other side of the membrane by the drainage body and emptied therefrom through the output aperture.

In order to avoid the liquid which has passed through the membrane escaping from the drainage body somewhere other than through the output aperture, the intake body has, around the membrane, a flange provided with a lip coming to rest on the drainage body in order to obtain the required sealing.

This makes it possibly notably, for example by collecting the liquid emptied through the output aperture in a graduated container, to know accurately the volume of the sample of liquid which has passed through the membrane.

EP 059 809 A discloses a disposable filtration unit for similar purposes but where the sample of liquid is not under pressure. This device comprises as intake body an open ended shell, and, as drainage body, a cup-shaped receptacle, a funnel-shaped support plate for the filtering membrane and a support pad laid on the support plate which is carried by an internal shoulder of the receptacle to which it can be permanently attached by a suitable cement or by ultrasonic welding. The lower end of the shell has a necked portion so that it can be received into a rim of the receptacle, the axial length of the necked portion and its position within the rim being such that there is some axial distance between the top of the receptacle rim and an edge of the necked portion. A plurality of vertical ribs are formed integral with the shell. These ribs have sufficient length to bridge this axial distance and can be attached to the upper end of the receptacle rim by ultrasonic welding so as to fix the shell to the receptacle. Because the attachment of the ribs to the receptacle occurs only at spaced intervals about the periphery of the receptacle, the ribs provides weak "breakaway" points so as to facilitate removal of the shell from the receptacle. In one embodiment, a flat, annular gasket is disposed between the lower end face of the shell and the support plate, the inner periphery of this gasket being squeezed between an inner foot of the shell and the filtering membrane whereas the outer periphery of the gasket is squeezed by an outer foot of the shell and rests on the rim of the support plate, this gasket thus providing, on the one hand, a liquid-tight seal between the shell and the filtering membrane and, on the other hand, an air-tight seal between the shell and the support plate. In other embodiments, the support plate comprises an upstanding tongue which is received between the inner foot and the outer foot of the shell whereas the flat, annular gasket is replaced by a gasket which has been put in a space between the rim and the tongue of the receptacle.

U.S. Pat. No. 4,678,576 A discloses a device for similar purposes, but not for a liquid under pressure. The disclosed device comprises, as intake body, an open ended upper body, and, as a drainage body, a cup-shaped receptacle and a support plate, a locking rim being further provided to lock the intake body and the drainage body. The support plate is sandwiched between an upper collar portion of a collar included in the receptacle and an internal shoulder of a necked portion including the upper body, the ring being engaged respectively, by its internal thread, with the external thread of the lower portion of the collar of the receptacle and, by an upper rim, with the lower external shoulder of a split flange included in the upper body. In one embodiment, two O-rings are provided respectively on one side and on the other of the support plate whereas in another embodiment, a single H-shaped gasket is provided The invention relates to a device of the same kind as known through French patent 2 677 664, but simpler, more convenient and more economical, both in manufacture and in use.

To that end it proposes a device for microbiological examination of a sample of liquid under pressure, having an intake body, a filtering membrane and a drainage body, said intake body having a reservoir, in one wall of which a liquid input aperture is made, said membrane closing said reservoir, said drainage body having means of supporting said membrane on the opposite side from said reservoir and a liquid output aperture, said intake body and said drainage body having integrally moulded mutual locking means; characterised in that said membrane is gripped annularly at the periphery between a first member forming part of said intake body and a second member forming part of said drainage body with one out of said first member and said second member having an elastomer seal by means of which it comes into contact with said membrane, and in that said locking means are adapted to allow the opening of said device by requiring only a separation movement between said first member and said second member, said locking means having means of axial latching between the intake body and the drainage body, one out of the latter having at least one axially oriented latching tab while the other has means of receiving said latching tab, which extends projecting from the edge of a skirt forming part of that one out of said intake body and said drainage body which includes it.

Thus, unlike the aforementioned earlier device known through French patent 2 677 664, where the locking means are constituted by thread elements, the opening of the device according to the invention is performed with no rotational movement between the intake body and the drainage body.

The device according to the invention therefore makes it possible to eliminate any risk of creasing the membrane at the time of opening the device where it is then in the wet state.

Furthermore, the elastomer seal, although it is present only on one of the faces of the membrane, makes it possible to obtain sealing on both faces of the membrane, that is to say both with the first member and with the second member, from the simple fact that said members grip the membrane, that is to say they are held close to one another, so that it is not necessary, in order to close the device according to the invention, to perform a rotational movement, unlike the above-mentioned earlier device known through French patent 2 677 664 which requires, so that the sealing lip on the intake body is applied with the required intensity on the drainage body, that assembly is carried out by screwing with a considerable torque.

The device according to the invention is therefore much simpler and more convenient to use than the above-mentioned earlier device known through French patent 2 677 664, and is furthermore simpler to manufacture, since there is no need, on the one hand, to make provision for achieving sealing between the membrane and the intake body by welding, and, on the other hand, sealing around the membrane between the intake body and the drainage body, given that, in the device according to the invention, the gripping of the membrane between the first member and the second member makes it possible to obtain these two instances of sealing directly.

Thanks to the fact that the locking means have means of axial latching between the intake body and the drainage body, the assembly of the device according to the invention is particularly simple, since it is sufficient to bring the intake body and the drainage body together in order to lock them by latching.

It should be noted that the elastomer seal, on account of its elasticity, takes up the play necessary for enabling latching, so that, once assembled, the intake body and the drainage body are held with no axial play with respect to one another.

The fact that one out of the intake body and the drainage body has at least one axially oriented latching tab while the other has means of receiving said latching tab, is preferred for reasons of simplicity and convenience, both in manufacture and in use.

Preferably, the membrane is held exclusively on account of it being gripped annularly at the periphery between said first member and said second member.

The manufacture and use of the device according to the invention are thus particularly simple, since no operation such as the sealing of the membrane existing in the earlier device has to be implemented, while, after opening of the device according to the invention, the membrane, which is fixed neither to the first member nor to the second member, can be recovered directly, for example with sterile tweezers in order to be put into culture in a conventional Petri dish.

Preferably again, said latching tab is connected to the remainder of that one out of said intake body and said drainage body which includes it, by a breakable zone.

The release of the locking means between the latching body and the drainage body can thus be performed by simple breaking of the latching tab, or even of a number of latching tabs if the device according to the invention has more than one.

According to other preferred characteristics, said drainage body has a circular table provided at its centre with means of supporting said membrane and having, around said support means, a wall having a surface situated facing said elastomer seal, which forms part of said intake body, said membrane being squeezed between said surface and said seal.

This arrangement offers in effect the advantage of being relatively simple to implement and of obtaining excellent results as regards sealing.

According to other preferred characteristics, for the same reasons, said output aperture of the drainage body is in the continuation of the internal passage of an output pipe disposed coaxially.

Preferably, said drainage body has, around said output pipe, an annular rib tapering towards its end.

This rib makes it possible in particular to drain the device according to the invention by placing it directly on a vacuum flask with said output pipe engaged in the central hole of the stopper of said flask and said annular rib resting on this stopper.

The invention also relates, in a second aspect, to a method for thus draining the device according to the invention.

The explanation of the invention will now be continued with the description of an example embodiment, given below as a non-limitative illustration, with reference to the accompanying drawings. In these:

FIG. 13 shows how the membrane is recovered with tweezers after this release; and FIG. 14 shows how the membrane is deposited in a Petri dish.

Figure 1:
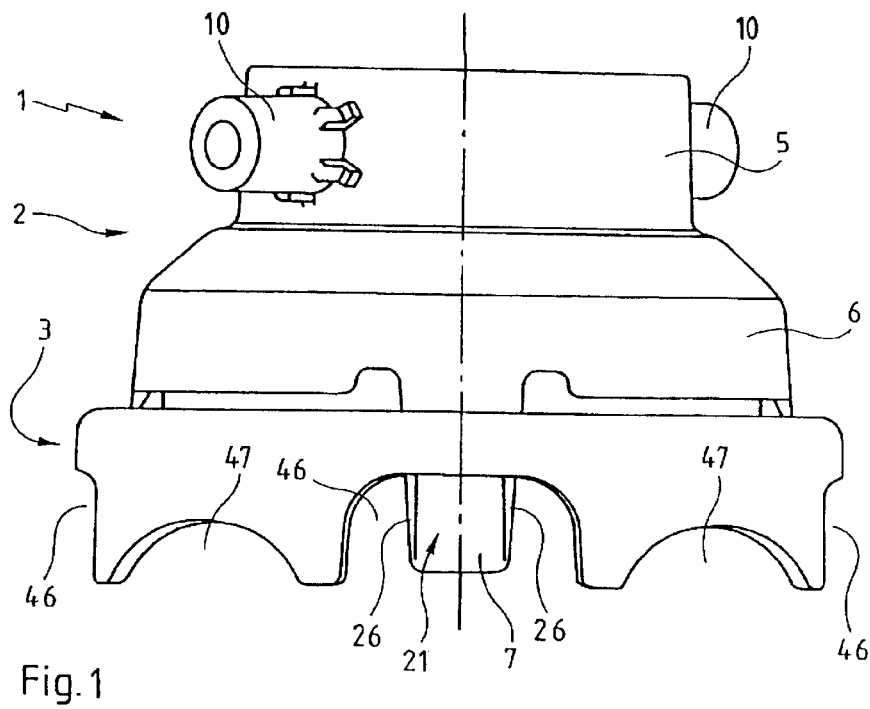
FIG. 1 is an elevational view of a device in accordance with the invention.
Figure 2:
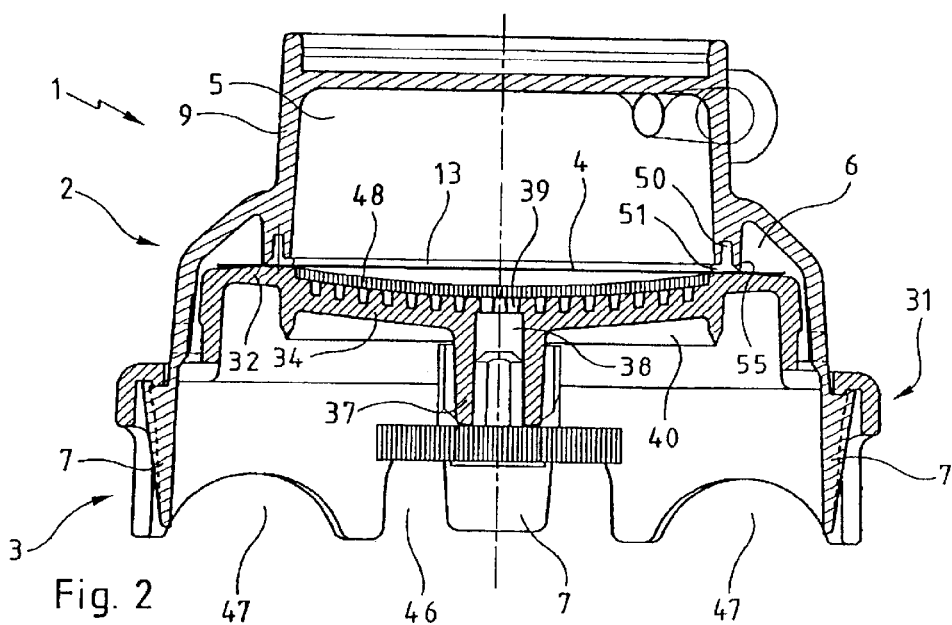
FIG. 2 is a sectional elevational view of this device.

The device 1 for microbiological examination of a sample of liquid under pressure shown in the drawings, and notably in FIGS. 1 and 2, has in general terms a symmetry of revolution around a central axis. It has an intake body 2, a drainage body 3 and a filtering membrane 4.

The intake body 2 has a reservoir 5, a skirt 6 which is connected externally to the reservoir 5 and four latching tabs 7 which extend projecting from the skirt 6, in an axial direction.

The reservoir 5 has an end wall 8 and a lateral wall 9.

Two diametrically opposite pipes 10 extend projecting outward from the lateral wall 9, above the skirt 6, each of these pipes constituting a female Luer connector adapted to receive internally a male Luer connector, as will be explained below with the help of FIG. 7, the passage internal to each pipe 10 being continued by an aperture 11 made in the wall 9, this aperture being in immediate proximity to the end wall 8.

Figure 3:
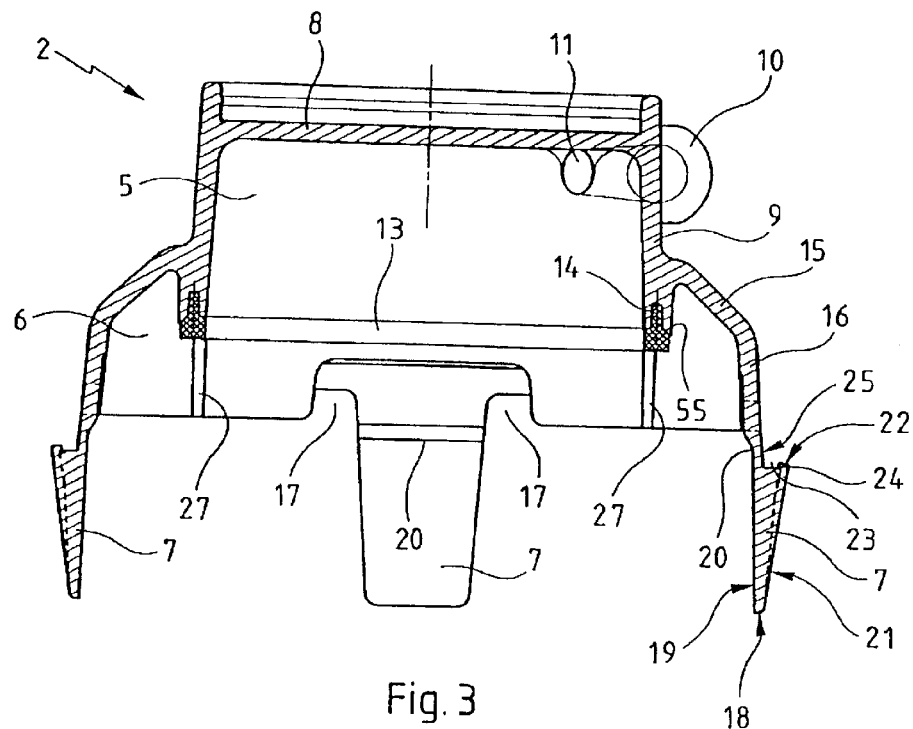
FIGS. 3 and 4 are similar views but showing, respectively, only the intake body and the drainage body.

The lateral wall 9 finishes at the end opposite the end wall 8 in an edge forming part of a seal 13, a groove 14 being made to that effect in the rigid part of the wall 9, as will be explained in more detail subsequently with the help of FIGS. 2, 3 and 6.

The skirt 6 is connected to the reservoir 5 by the outside of the lateral wall 9, at a level situated between the groove 14 and the pipes 10, the skirt 6 having a truncated-cone shaped wall 15 and a cylindrical wall 16, the skirt 6 being connected to the wall 9 by the small-diameter end of the wall 15 while the connection between the walls 15 and 16 is made by the large-diameter end of the wall 15, the connection between the walls 15 and 16 being situated approximately at the level of the edge of the wall 9.

Each of the latching tabs 7 has a general outline in the form of a trapezium symmetrical with respect to the axial direction, the side forming the free end 18 of the tab 7 being parallel to the one by which this tab is connected to the skirt 6, and more precisely to the edge of the wall 16, the tab 7 narrowing steadily between its connection to the skirt 6 and its free end.

On either side of each tab 7, a notch 17 is made in the wall 16, over a certain distance from the edge thereof.

Each tab 7 has, from its free end 18, an internal surface 19 which is straight, that is to say parallel to the axial direction, as far as a dihedral 20 from which the surface 19 is inclined inward and towards the wall 16.

As for the external surface 21 of each tab 16, this is inclined outward and towards the wall 16, the surface 21 extending between the surface 18 and a transversely oriented surface 22 which connects the surface 21 and a groove 23 situated between an external shoulder 24 whose surface 22 constitutes the edge and a surface 25 offset inward with respect to the surface 21, the surface 25 being in the continuation of the external surface of the wall 16.

It should be noted that the portion of each tab 7 situated between the bottom of the groove 23 and the edge of the wall 16 has a thickness which is a minimum at the level of the dihedral 20.

Consequently, it is in the region of the dihedral 20 that the tab 7 breaks if a sufficiently large pressure is exerted on the surface 21, and more generally if there is exerted on the tab 7 a radial force directed inward, the force necessary for breaking the tab 7 being smaller the closer it is applied to the end surface 18.

As can be seen more particularly in FIG. 1, the surface 21 has edges parallel to the axial direction, each tab 7 having a notch 26 with an L-shaped profile between the lateral edges of the surface 21 and the lateral edges of the tab 7.

Figure 4:
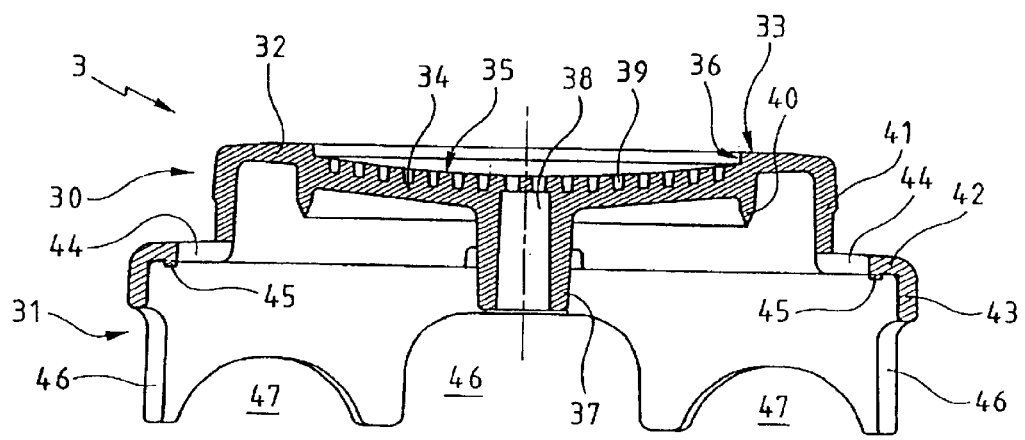

As can be seen better in FIG. 4, the drainage body 3 has a circular table 30 and a skirt 31 disposed in a step around the table 30.

The latter has an annular transverse wall 32 delimited on the opposite side from the skirt 31 by a surface 33 which is flat in the main but having a slight bevel towards the outside.

The internal periphery of the wall 32 is connected to a wall 34 delimited, on the side of the surface 33, by a surface 35 which is concave in the main, offset with respect to the surface 32 in the axial direction, towards the skirt 31, the perimeter of the surface 35 and the internal periphery of the surface 33 being connected by a slightly truncated-cone shaped surface 36.

The wall 34 is connected centrally to a pipe 37 whose internal passage is extended into the wall 34 by an output aperture 38, concentric drainage channels 39 being put into the wall 34 from the surface 35, radially oriented channels (not visible in the drawings) also being made, with the same depth as the channels 39, these radial channels opening of course into the output aperture 38, through which, therefore, there flows out all the liquid drained by the channels made in the wall 34 hollowed out with respect to the surface 35.

At the junction between the walls 32 and 34 there is situated an annular rib 40 which projects with respect to the walls 32 and 34 on the side of the skirt 31, this rib tapering towards its free end in a V-shaped profile, so that this end constitutes a sharp edge.

The table 30 also has a tubular lateral wall 41 which is connected by one end to the wall 32 while, by the other end, it is connected to the skirt 31.

The latter has a transversely oriented annular wall 42 and an axially oriented cylindrical wall 43, the wall 42 being connected by one of its ends to the wall 41 and by the other to the wall 43.

In the wall 42, in proximity to the wall 41, four openings 44 are made, which have between them the same angular spacing as between the latching tabs 7, that is to say they are spaced out from one another by 90°, these openings having an outline corresponding to the largest outline of the tabs 7, so that the latter can each pass through a respective opening 44.

Each opening 44 is bordered on the external side by an axially oriented tooth 45 projecting on the opposite side from the table 30.

Figure 5:
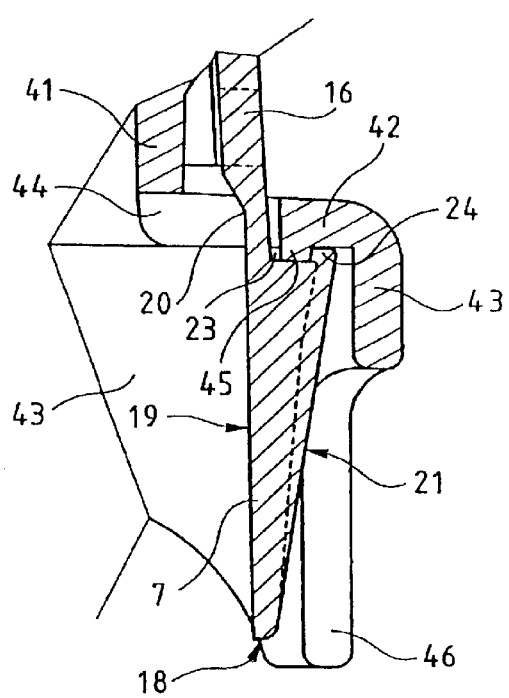
FIG. 5 is an enlargement of the part of FIG. 2 situated at the bottom right.

Each tooth 45 extends projecting over a height corresponding to the depth of the groove 23 and has a thickness less than the width of the groove 23, the distance separating each tooth 45 from the wall 43 being greater than the thickness of the shoulder 24 (see FIG. 5).

At the level of each opening 44, the wall 43 has a notch 46 of general rectangular form with rounded corners, extending over approximately two thirds of the height of the wall 43 and over a width which is approximately twice the width of the latching tabs 7.

The wall 43 also has four notches 47, each disposed halfway between two successive notches 46, the notches 47 having a rounded form whose maximum height corresponds approximately to one third of the height of the wall 43.

The drainage body 3 also has a porous pad 48 (not depicted in FIG. 4), which has a constant thickness with two opposite surfaces of the same form as the surface 35, its diameter and thickness being the same as those of the surface 36.

When the filtration body 2, the drainage body 3 and the membrane 4 are assembled, as shown notably in FIGS. 1 and 2, the membrane 4 is gripped between the edge of the lateral wall 9 of the reservoir 5 of the intake body 2 and the surface 33 of the wall 32 of the circular table 30 of the drainage body 3, the bodies 2 and 3 being locked to one another by virtue of the latching tabs 7 and the skirt 31, which are mutually disposed as can be seen more particularly in FIG. 5.

It should be noted that the tooth 45 of the wall 42 fits into the groove 23 of the tab 7 and that the shoulder 24 of this tab fits into the space situated between the wall 43 and the tooth 45, so that the cooperation between the shoulder 24 and the tooth 45 provides an extremely powerful locking of the tab 7 in the skirt 31, capable of withstanding relatively large forces tending to move the bodies 2 and 3 away from one another.

It should also be noted that the end 18 of the tab 7 is recessed with respect to the free end of the wall 43, so that, when the device 1 is put down on a surface with the drainage body 3 at the bottom, it is by means of the skirt 31 thereof that the device 1 rests on this surface, no force being exerted for this reason on the tabs 7, which therefore do not risk being broken accidentally.

Figure 6:
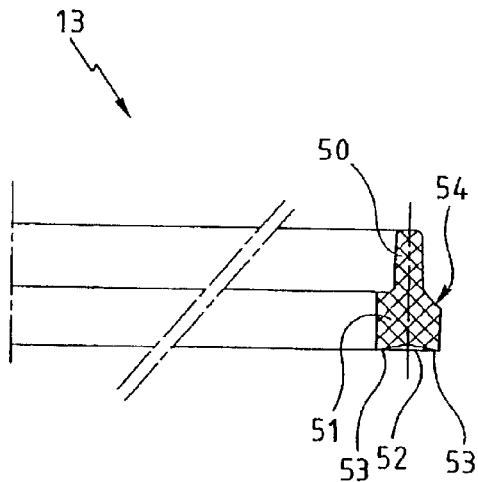
FIG. 6 is a partial sectional elevational view of the seal with which the intake body is provided.

As can be seen in FIG. 2, when the device 1 is assembled, the seal 13, and more particularly the cushion thereof, is highly compressed compared with the off-load form of this seal shown in FIG. 6.

As indicated above, this seal has a T-shaped general profile whose longitudinal branch forms a rib 50 designed to be inserted into the groove 14 and whose transverse branch forms a cushion 51 designed to enter into contact with the membrane 4.

The free end of the cushion 51 has a central slot 52 which makes it possible to release two annular lips 53 allowing the best cooperation of the cushion 51 with the membrane 4.

It should be noted that the junction between the rib 50 and the cushion 51 is made by a straight surface on the internal side while, on the external side, there is a bevel 54.

This bevel in fact corresponds to a chamfered lip 55 at the external periphery of the end of the rigid part of the wall 9, this chamfered lip making it possible to laterally contain the cushion 51 on the external side in order that it flows mainly inward, that is to say towards the chamber delimited by the membrane 4 and the reservoir 5.

The intake body 2 is obtained, with the exception of the seal 13, by moulding of a relatively rigid and transparent plastic, and then there is moulded, on to this piece, the seal 13, which is made of elastomer, this over-moulding being carried out in the example illustrated by bi-injection.

The part of the drainage body 3 depicted in FIG. 4 is also made of relatively rigid moulded plastic, here white in colour, this part being next equipped, by simple fitting, with the porous pad 48.

In order to assemble the intake body 1, the drainage body 3 and the membrane 4, the latter is put on the table 30, concentrically therewith, then the intake body 2 is positioned facing the drainage body 3 with the latching tabs 7 aligned with the openings 44, then the body 2 is pressed hard towards the body 3 so that the tabs 7 engage in the openings 44 flexing slightly by virtue of the inclined surface 21 which acts as a ramp, the force exerted allowing the surface 22 of the shoulder 24 to get over the tooth 45 at the end of the pushing in movement, by virtue of the spring of the tabs 7, the seal 13 next relaxing slightly so that the play between the tabs 7 and the skirt 31 is completely taken up, the elasticity of the seal 13, which is then compressed, maintaining the locking thus obtained.

It should be noted that the maintaining of the seal in the compressed state allows it to offer excellent sealing between the membrane 4 and the edge of the wall 9, and furthermore, by reaction, between the membrane 4 and the surface 33.

It should also be noted that the internal surface of the wall 16 has localized areas of extra thickness 27 (FIG. 3) coming into contact with the external surface of the wall 41, which provides a lateral wedging between these surfaces, which are of similar diameter, and more generally between the bodies 2 and 3.

Finally it should be noted that, once the device 1 has been assembled in this way, it is possible to package it and sterilize it with a gas such as ETO or by irradiation.

Of course, before packaging the assembled device 1 and sterilizing it, each of the pipes 10 and 37 is equipped with a stopper.

There will now be explained how the sampling of a liquid under pressure is carried out with the device 1.

Figure 7:
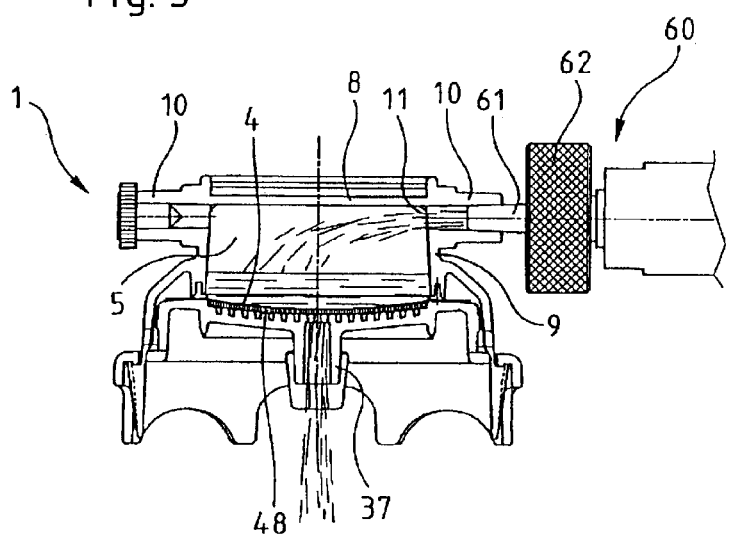
FIG. 7 is a sectional elevational view showing how the device according to the invention is used for sampling the liquid to be examined.

First of all the stopper blocking off one of the pipes 10 and the stopper blocking off the pipe 37 are removed, then the unstoppered pipe 10 is connected to a source of liquid under pressure, for example using, as shown in FIG. 7, a sampling connector 60 having a male Luer tip 61, which is inserted into the passage of the unstoppered pipe 10 and the valve 62 of the connector 60 is manipulated, so that the chamber formed by the reservoir 5 and the membrane 4 is raised to the same pressure as the liquid, for example 3 bars, the liquid entering the reservoir 5 through the aperture 11 and leaving the reservoir by passing through the membrane 4, which comes to rest on the porous pad 48, the liquid which has passed through the membrane 4 being guided by the channels 39 to the aperture 38, the liquid leaving the device 1 by the pipe 37, a graduated container being preferably disposed under the device 1 in order to recover the liquid coming out of the pipe 37 in order to know when the volume required for the sample has passed through the membrane 4.

When this volume has been reached, the valve 62 is closed and the device 1 is removed from the connector 60, then there is put in place, in the unstoppered pipe 10, an air sterilization filter 63 (depicted in FIG. 10 but not in FIG. 8), and the drainage of the liquid still present notably in the reservoir 5 is next carried out, by suction through the output aperture 38.

Figure 8:
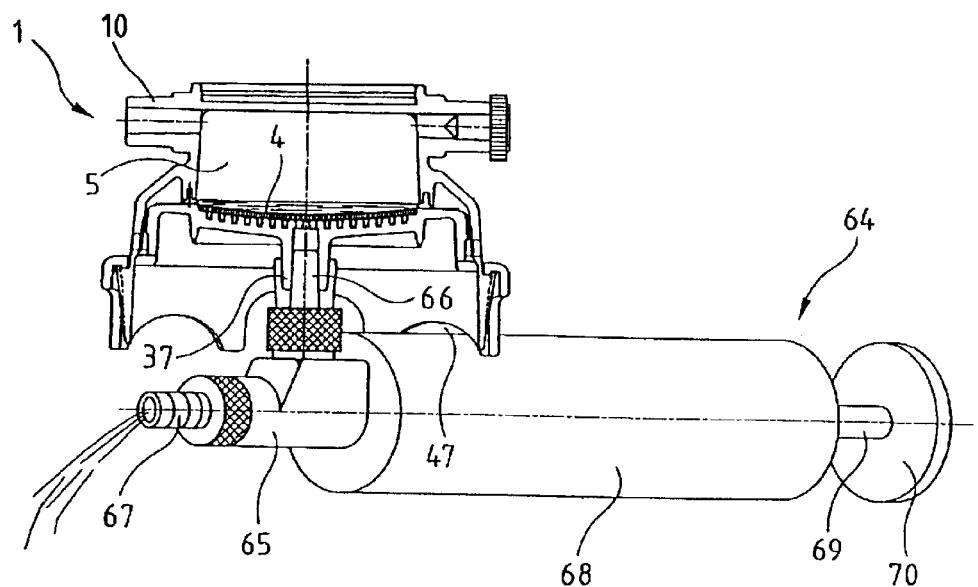
FIG. 8 is a similar view showing how the device in accordance with the invention is drained, after a sample has been taken, by means of a syringe.
Figure 9:
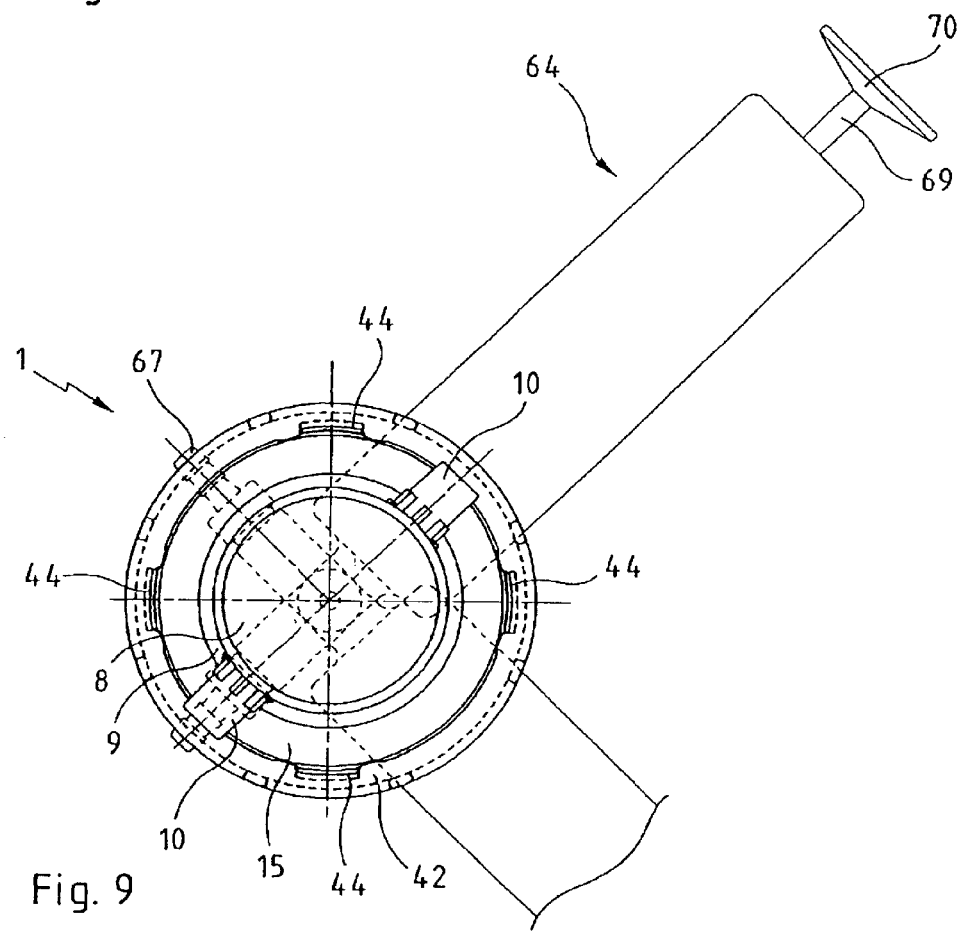
FIG. 9 is the corresponding top view, a second possible location for the syringe being shown with a syringe partially illustrated.

In the example shown in FIG. 8, the drainage is performed with a syringe or pump 64 having a connector 65 provided with a suction tip 66 which has been inserted into the passage of the pipe 37, the liquid sucked out by the tip 66 being expelled by the tip 67 when the shaft 69 is pushed into the body 68, by pressing on the plunger 70.

It should be noted that the notches 47 made in the wall 43 make it possible to correctly position the pump or syringe 64 in relation to the device 1, in four positions at 90° from one another, two of these positions being shown in FIG. 8.

Figure 10:
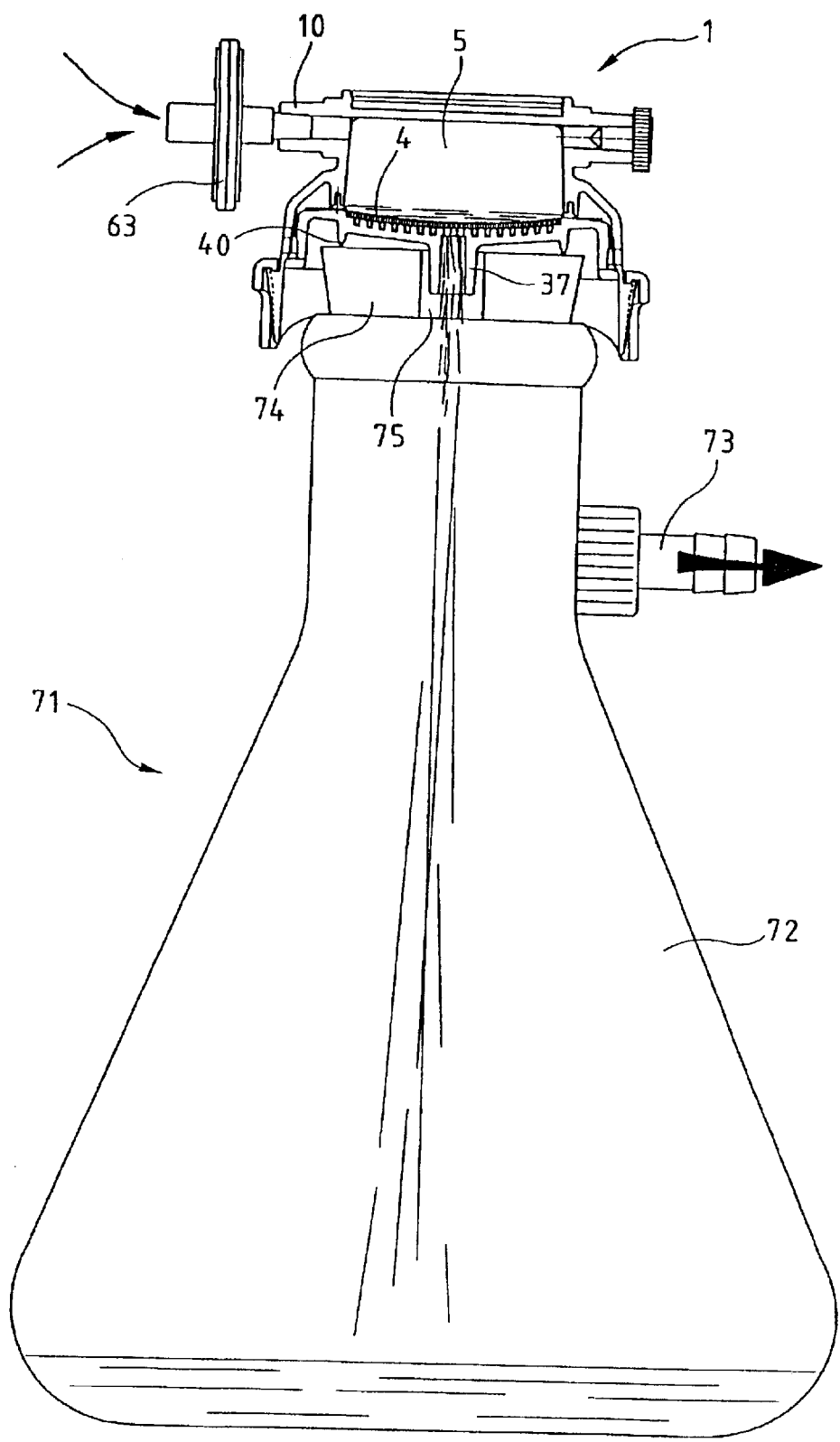
FIG. 10 is a view similar to FIG. 8, where the drainage is performed with a vacuum flask.

Another possibility for extracting the liquid remaining in the device 1 after sampling, is to use a vacuum flask, as shown in FIG. 10.

The vacuum flask 71 illustrated has a glass body 72 having, at the level of its neck, a pipe 73 connected, in a manner not depicted, to a vacuum pump, and, at the top of this neck, a flexible stopper 74 with a central aperture 75 made in it, the flask 71 being of a type which is commonly found in practice.

The device 1 is simply put down on the stopper 74, with the pipe 37 engaged in the aperture 75 and the rib 40 supported on the top of the stopper 74.

On account of the tapered profile of the rib 40, the latter locally deforms the stopper 74 and provides sealing which makes it possible to suck out the residual liquid, as drawn.

Figure 11:
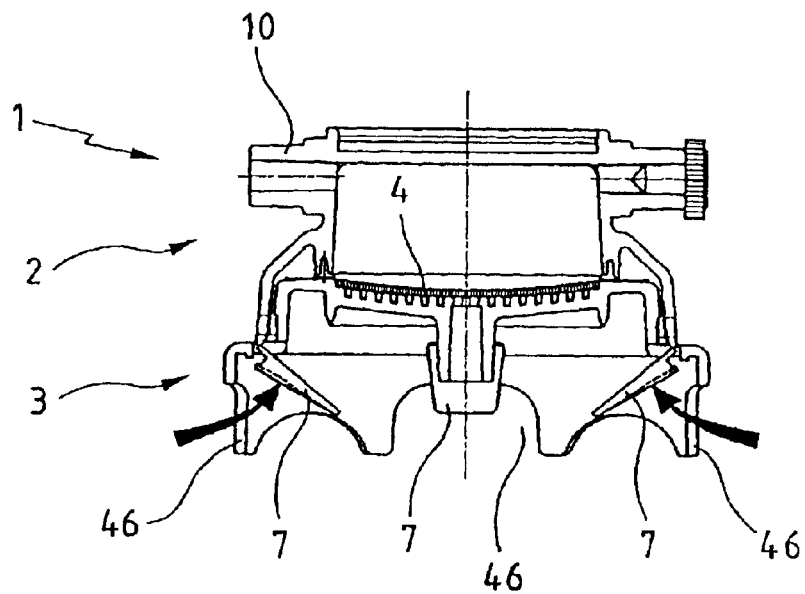
FIGS. 11 and 12 are sectional elevational views showing how the latching tabs are broken off the intake body in order to release the latter from the drainage body.
Figure 12:
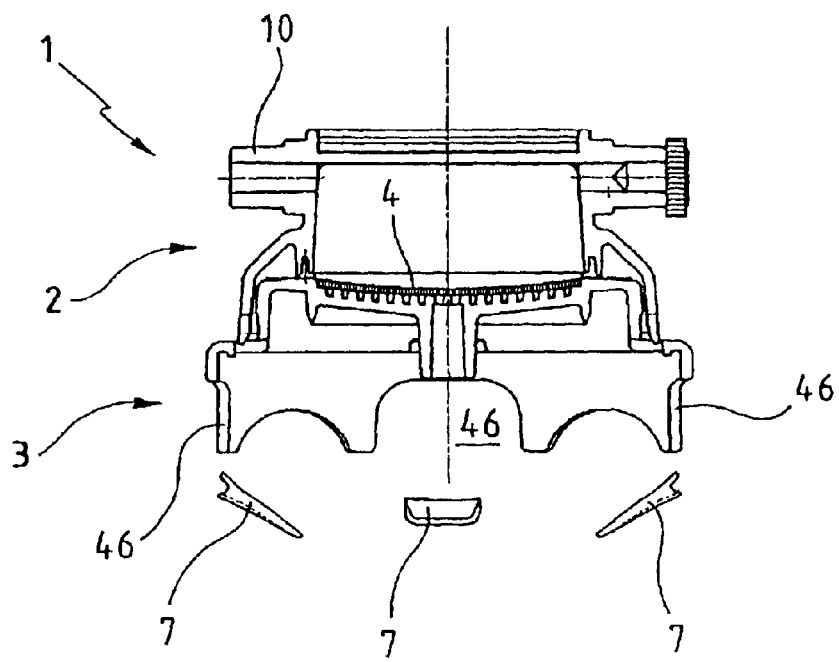

Once the liquid remaining in the device 1 has been emptied therefrom, the device 1 can be opened, which is performed by breaking the four latching tabs 7, by simple pressure on said tabs through the respective notches 46, as explained above and illustrated in FIGS. 11 and 12.

It is then possible to remove the intake body 2 from the drainage body 3 and pick up the membrane 4, for example with sterile tweezers 80, as shown in FIG. 13, then deposit the membrane through which the sample to be examined has passed, in a Petri dish 81, as shown in FIG. 14, then carry out conventionally the incubation of the membrane/Petri dish assembly.

It should be noted that the concavity of the surface 35 has been calculated so that the ratio of the difference between the length of the arc corresponding to the profile, in a diametral plane, of the surface of the pad 48 facing the membrane 4 and between the length of the chord of this arc, over the latter length, corresponds to the coefficient of expansion of the membrane 4 between the dry state and the wet state.

The result thereof is that the expansion of the membrane 4, when it changes from the dry state to the wet state, corresponds precisely to the difference in length between the arc corresponding to the above-mentioned profile and the chord of this arc, so that, in the wet state, the membrane 4 rests perfectly on the pad 48, with no creases. The pad 48 therefore provides a particularly effective support for the membrane 4 when it is subjected to the difference in pressure which allows the liquid to flow through it.

Moreover, when the user recovers the membrane 4 with the tweezers 80 as shown in FIG. 13, this membrane has a concave form, on the side where the reservoir 5 is situated, that is to say on the side where any micro-organisms retained by the membrane at the time of sampling are present, the curvature of the membrane 4 thus being in the correct direction where putting it down on the surface of the culture medium 82 in the dish 81 is concerned.

This is because, when the membrane 4 is positioned on the dish 81, it is the convex side of the membrane 4 which faces the surface of the medium 82, so that, putting down the membrane 4 on the medium 82 from a portion of the membrane opposite the tweezers 80 and moving them so that the membrane progressively comes into contact with the medium 82 to the place where it is held by the tweezers. The risk that the membrane has one or more hollows on the opposite side from the medium 82, and therefore the risk that it develops one or more pocket(s) of air between the membrane 4 and the medium 82, are thus zero or at any rate minimal.

The culture medium 82 in the dish 81 illustrated in FIG. 14 is a culture medium containing agar—agar, used in the solid state after having been poured into the dish hot.

If it is wished to use a liquid culture medium, it is possible to replace the Petri dish 81 with a similar dish but one where the agar—agar culture medium 82 is replaced by an absorbent pad impregnated with liquid culture medium.

Another possibility, rather than culturing the micro-organisms outside the device 1, is to inject liquid culture medium therein using one of the pipes 10, then to drain the excess culture medium using the pipe 37, and to next put the device 1 to incubate directly, the membrane 4 being recovered only in order to identify and count the micro-organisms after incubation.

In such a case, there is an advantage in using a liquid culture medium which is slightly more concentrated than the conventional media since there always remains, notably in the pad 48, a certain amount of the sampled liquid which mixes with the injected culture medium which is therefore diluted.

In variants, not depicted, it is the drainage body 3, and not the intake body 2, which has the elastomer seal such as the seal 13 described above; the male and female latching elements between the bodies 2 and 3 are provided respectively on the drainage body 3 and the intake body 2, rather than the reverse; and/or use is made of latching means of different type, locking means having hinge means between the bodies 2 and 3 and latching means opposite the hinge means, or means of locking other than by latching.

Many other variants are possible depending on circumstances, and it should be stated in this respect that the invention is not limited to the examples described and depicted.

What is claimed is:

1. A device for microbiological examination of a sample of liquid under pressure, having an intake body, a filtering membrane and a drainage body, said intake body having a reservoir, the reservoir having an endwall and a lateral wall, the lateral wall having a liquid input aperture, said membrane closing said reservoir so as to form a chamber for liquid entering the chamber through the input aperture and exiting through the membrane, said drainage body having means of supporting said membrane on the opposite side from said reservoir and a liquid output aperture, said intake body and said drainage body having integrally moulded mutual locking means; comprising in that said membrane is gripped annularly at the periphery between a first member forming part of said intake body and a second member forming part of said drainage body with one out of said first member and said second member having an elastomer seal by means of which it comes into contact with said membrane, and in that said locking means are adapted to allow the opening of said device by requiring only a separation movement between said first member and said second member, said locking means having means of axial latching between the intake body and the drainage body, the intake body having at least one axially oriented latching tab while the drainage body has means of receiving said latching tab, said means of receiving said latching tab being a hole formed in a transversely oriented annular wall connected at one end to a first axially oriented wall and at the other end to a second axially oriented wall which extends projecting from the edge of a skirt forming part of the drainage body.

2. A device according to claim 1 wherein the membrane is held exclusively on account of it being gripped annularly at the periphery between said first member and said second member.

3. A device according to claim 1 wherein the seal is moulded on to that one out of said first member and said second member which includes it.

4. A device according to claim 1 wherein the first member has said elastomer seal moulded to it.

5. A device according to claim 1 wherein the first member has said elastomer seal moulded to it and said first member forms a lateral wall of said reservoir of the intake body, said wall finishing at one end in an edge forming part of said seal.

6. A device according to claim 1 wherein the first member which has said elastomer seal moulded to it and said first member forms a lateral wall of said reservoir of the intake body, said wall finishing at one end in an edge forming part of said seal and a groove is made at the end of a rigid part of said lateral wall while said seal has a T-shaped profile whose longitudinal branch forms a rib inserted into said groove and whose transverse branch forms a cushion which is in contact with the membrane.

7. A device according to claim 1 wherein the first member has said elastomer seal moulded to it and said first member forms a lateral wall of said reservoir of the intake body, said wall finishing at one end in an edge forming part of said seal and a groove is made at the end of a rigid part of said lateral wall while said seal has a T-shaped profile whose longitudinal branch forms a rib inserted into said groove and whose transverse branch forms a cushion which is in contact with the membrane and there is a bevel between the rib and the cushion on the external side, while, on the internal side, the rib and the cushion are connected by a straight surface.

8. A device according to claim 1 wherein the first member has said elastomer seal moulded to it and said first member forms a lateral wall of said reservoir of the intake body, said wall finishing at one end in an edge forming part of said seal and a groove is made at the end of a rigid part of said lateral wall while said seal has a T-shaped profile whose longitudinal branch forms a rib inserted into said groove and whose transverse branch forms a cushion which is in contact with the membrane and said cushion has two annular lips.

9. A device according to claim 1 wherein said latching tab is connected to the remainder of that one out of said intake body and said drainage body which includes it, by a breakable zone.

10. A device according to claim 1 wherein said latching tab is connected to the remainder of that one out of said intake body and said drainage body which includes it, by a breakable zone and said breakable zone is situated in the region of a dihedral in one of the surfaces of said latching tab.

11. A device according to claim 1 wherein said latching tab is connected to the remainder of that one out of said intake body and said drainage body which includes it, by a breakable zone and said breakable zone is situated in the region of a dihedral in one of the surfaces of said latching tab and said surface having a dihedral is situated on the internal side of the latching tab.

12. A device according to claim 1 wherein one out of said intake body and said drainage body which has means of receiving said latching tab has a wall oriented transversely and provided with an opening through which the latching tab can pass, means being provided for preventing the withdrawal of the tab once it has been pushed right into the opening.

13. A device according to claim 1 wherein one out of said intake body and said drainage body which has means of receiving said latching tab has a wall oriented transversely and provided with an opening through which the latching tab can pass, means being provided for preventing the withdrawal of the tab once it has been pushed right into the opening and said means for preventing the withdrawal of the latching tab are provided on the latter and on said wall.

14. A device according to claim 1 wherein one out of said intake body and said drainage body which has means of receiving said latching tab has a wall oriented transversely and provided with an opening through which the latching tab can pass, means being provided for preventing the withdrawal of the tab once it has been pushed right into the opening and said means for preventing the withdrawal of the latching tab are provided on the latter and on said wall and said means for preventing the withdrawal of the latching tab have, on said wall, a tooth oriented axially and bordering said opening and having, on said latching tab, a groove adapted to accommodate said tooth.

15. A device according to claim 1 wherein one out of said intake body and said drainage body which has means of receiving said latching tab has a wall oriented transversely and provided with an opening through which the latching tab can pass, means being provided for preventing the withdrawal of the tab once it has been pushed right into the opening and said transversely oriented wall is connected to a lateral wall extending on the opposite side from that one out of said intake body and said drainage body which has the latching tab, with the dimension in the axial direction of said lateral wall greater than the dimension in the axial direction of the latching tab.

16. A device according to claim 1 wherein a notch is made in said lateral wall at opening, to make it possible to press on said latching tab.

17. A device according to claim 1 wherein one out of said intake body and said drainage body has a number of said latching tabs.

18. A device according to claim 1 wherein said locking means comprise exclusively said axial latching means.

19. A device according to claim 1 wherein said drainage body has a circular table provided at its centre with means of supporting said membrane and having, around said support means, a wall having a surface situated facing said elastomer seal, which forms part of said intake body, said membrane being squeezed between said surface and said seal.

20. A device according to claim 1 wherein said drainage body has a circular table provided at its centre with means of supporting said membrane and having, around said support means, a wall having a surface situated facing said elastomer seal, which forms part of said intake body, said membrane being squeezed between said surface and said seal and the external diameter of said circular table corresponds substantially to the internal diameter of a skirt included in said intake body, said skirt encircling said circular table.

21. A device according to claim 1 wherein said drainage body has a circular table provided at its centre with means of supporting said membrane and having, around said support means, a wall having a surface situated facing said elastomer seal, which forms part of said intake body, said membrane being squeezed between said surface and said seal and the external diameter of said circular table corresponds substantially to the internal diameter of a skirt included in said intake body, said skirt encircling said circular table and areas of extra thickness for wedging are provided between said circular table and said skirt.

22. A device according to claim 1 wherein said drainage body has a circular table provided at its centre with means of supporting said membrane and having, around said support means, a wall having a surface situated facing said elastomer seal, which forms part of said intake body, said membrane being squeezed between said surface and said seal and said drainage body has a skirt disposed in a step with respect to said circular table.

23. A device according to claim 1 wherein said drainage body has a circular table provided at its centre with means of supporting said membrane and having, around said support means, a wall having a surface situated facing said elastomer seal, which forms part of said intake body, said membrane being squeezed between said surface and said seal and said drainage body has a skirt disposed in a step with respect to said circular table and said skirt has means of latching with said intake body.

24. A device according to claim 1 wherein said drainage body has a circular table provided at its centre with means of supporting said membrane and having, around said support means, a wall having a surface situated facing said elastomer seal, which forms part of said intake body, said membrane being squeezed between said surface and said seal and said drainage body has a skirt disposed in a step with respect to said circular table and said skirt of the drainage body has at least one notch adapted to allow the placing of a drainage syringe.

25. A device according to claim 1 wherein said output aperture of the drainage body is in the continuation of the internal passage of a coaxially disposed output pipe.

26. A device according to claim 1 wherein said output aperture of the drainage body is in the continuation of the internal passage of a coaxially disposed output pipe and said drainage body has, around said output pipe, an annular rib tapering towards its end.

27. A method for draining a device according to claim 1 wherein said output aperture of the drainage body is in the continuation of the internal passage of a coaxially disposed output pipe and said drainage body has, around said output pipe, an annular rib tapering towards its end and it is placed on a vacuum flask with said output pipe engaged in the central hole of the stopper of said flask and said annular rib resting on this stopper.

28. A device for microbiological examination of a sample of liquid under pressure, having an intake body, a filtering membrane and a drainage body, said intake body having a reservoir, the reservoir having an endwall and a lateral wall, the lateral wall having a liquid input aperture, said membrane closing said reservoir so as to form a chamber for liquid entering the chamber through the input aperture and exiting through the membrane, said drainage body having means of supporting said membrane on the opposite side from said reservoir and a liquid output aperture, said intake body and said drainage body having integrally moulded mutual locking means; comprising in that said membrane is gripped annularly at the periphery between a first member forming part of said intake body and a second member forming part of said drainage body with one out of said first member and said second member having an elastomer seal by means of which it comes into contact with said membrane, and in that said locking means are adapted to allow the opening of said device by requiring only a separation movement between said first member and said second member, said locking means having means of axial latching between the intake body and the drainage body, the drainage body having at least one axially oriented latching tab while the intake body has a means of receiving said latching tab, said means of receiving said latching tab being a hole formed in a transversely oriented annular wall connected at one end to a first axially oriented wall and at the other end to a second axially oriented wall which extends projecting from the edge of a skirt forming part of said intake body.

* * * * *